US012751619B2

(12) United States Patent
Lee et al.

(10) Patent No.: US 12,751,619 B2
(45) Date of Patent: Oct. 6, 2026

(54) INTRAOCULAR PRESSURE SENSING DEVICE AND METHOD USING SENSOR BASED ON HALF WHEATSTONE BRIDGE

(71) Applicant: Research & Business Foundation SUNGKYUNKWAN UNIVERSITY, Suwon-si (KR)

(72) Inventors: Yoonmyung Lee, Suwon-si (KR); Donguk Seo, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 563 days.

(21) Appl. No.: 18/217,684

(22) Filed: Jul. 3, 2023

(65) Prior Publication Data

US 2024/0000313 A1 Jan. 4, 2024

(30) Foreign Application Priority Data

Jul. 4, 2022 (KR) ........................ 10-2022-0081976

(51) Int. Cl.
*A61B 3/16* (2006.01)
*A61F 9/007* (2006.01)

(52) U.S. Cl.
CPC ............ *A61B 3/16* (2013.01); *A61F 9/00781* (2013.01); *A61B 2562/0247* (2013.01)

(58) Field of Classification Search
CPC ............... A61B 3/16; A61B 2562/0247; A61F 9/00781
See application file for complete search history.

(56) References Cited

U.S. PATENT DOCUMENTS 7,398,688 B2 * 7/2008 Zdeblick ................. G01L 9/065 73/700
9,429,479 B2 * 8/2016 Millar ................ A61B 5/14539
(Continued)

FOREIGN PATENT DOCUMENTS

KR 10-1376677 B1 3/2014
KR 10-2017-0058811 A 5/2017
(Continued)

OTHER PUBLICATIONS

Korean Office Action issued on May 27, 2024, in counterpart Korean Patent Application No. 10-2022-0081976 (6 pages in English, 6 pages in Korean).

*Primary Examiner* — Devin B Henson
(74) *Attorney, Agent, or Firm* — NSIP Law

(57) ABSTRACT

According to an exemplary embodiment of the present disclosure, a pressure sensing device using a sensor based on a Wheatstone bridge includes: a half Wheatstone bridge unit including two variable resistors of which resistance values are changed according to an environmental change; a variable capacitor unit electrically connected to the half Wheatstone bridge unit and generating RC delays for two variable resistors, respectively; an amplifier amplifying respective charging voltages charged after a time of the respective RC delays; and a comparator comparing the amplified charging voltages and outputting the compared charging voltages as digital values. As a result, an intraocular pressure sensing device is further miniaturized and has smaller power loss.

19 Claims, 8 Drawing Sheets

200

(56) References Cited

U.S. PATENT DOCUMENTS

| | | | | |
|---|---|---|---|---|
| 2005/0119636 | A1 * | 6/2005 | Haffner .................... | A61B 3/16<br>623/4.1 |
| 2012/0289810 | A1 | 11/2012 | Ehrecke | |
| 2020/0201504 | A1 * | 6/2020 | Park ........................ | G06F 3/045 |
| 2020/0305741 | A1 | 10/2020 | Gunn et al. | |

FOREIGN PATENT DOCUMENTS

| | | | |
|---|---|---|---|
| KR | 10-2020-0078992 | A | 7/2020 |
| WO | WO 2015/117015 | A1 | 8/2015 |

* cited by examiner

【FIG. 1A】 PRIOR ART
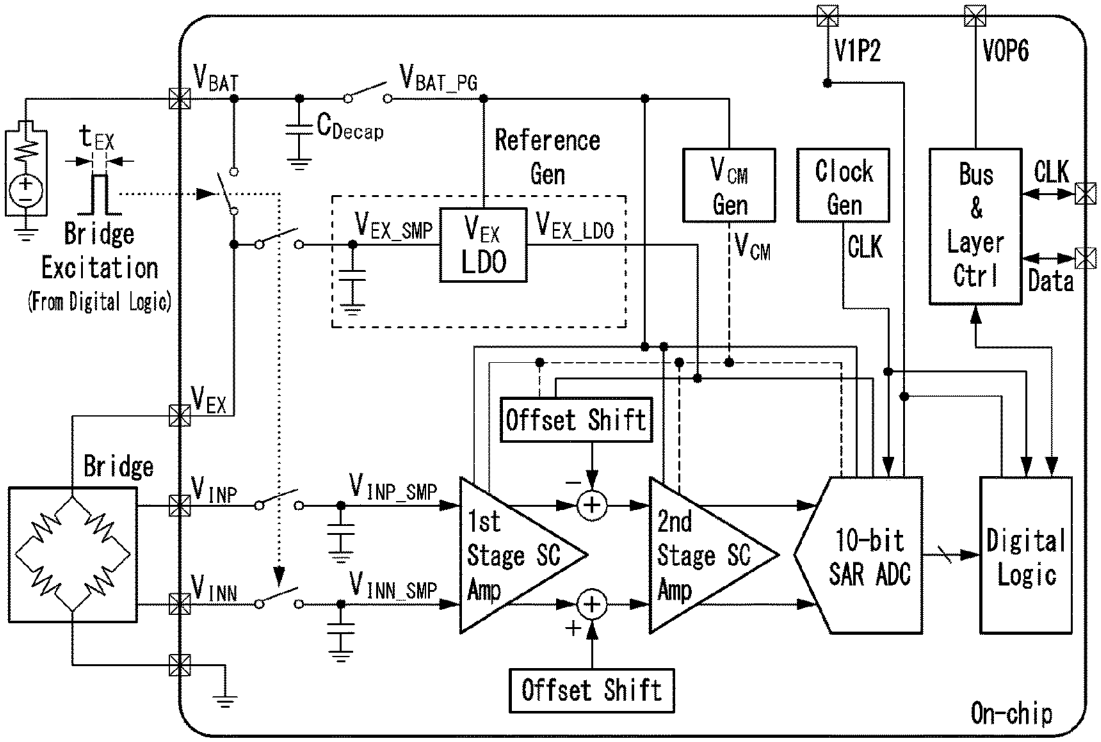
【FIG. 1B】 PRIOR ART
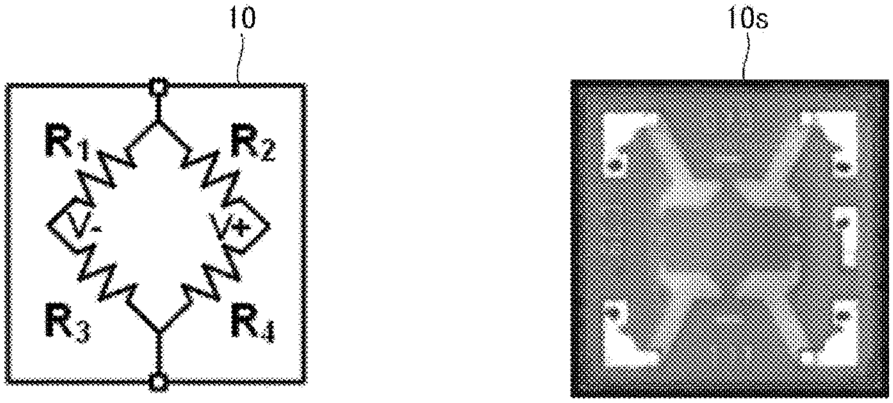

【FIG. 1C】PRIOR ART
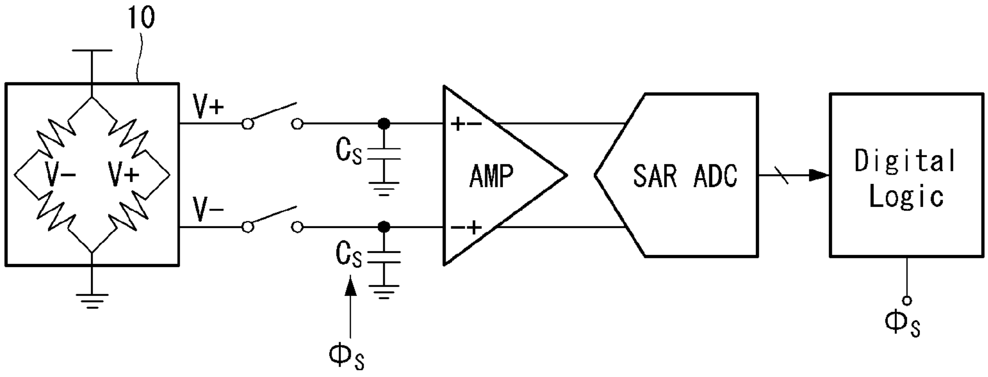
【FIG. 2A】
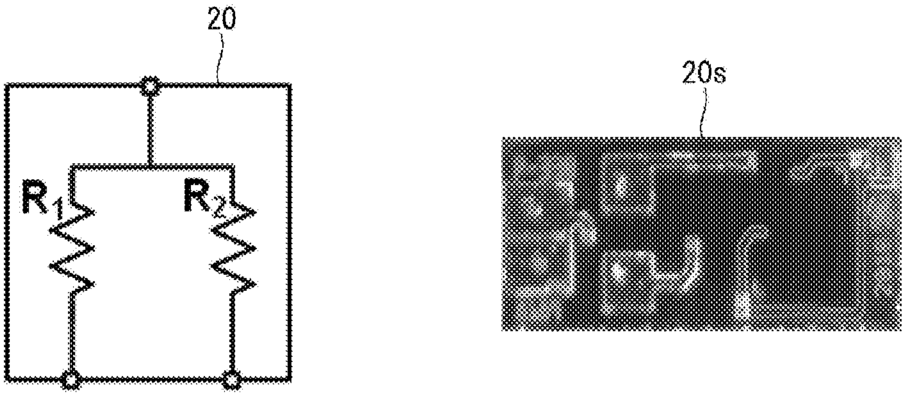

【FIG. 2B】
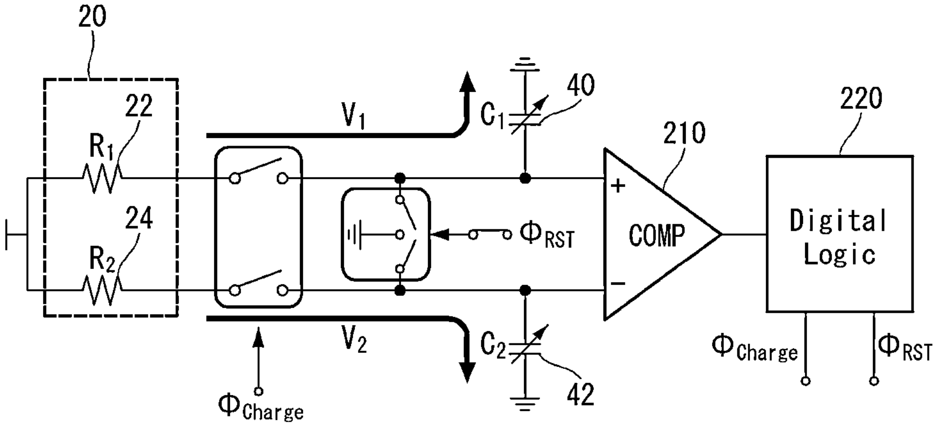
200

【FIG. 3】
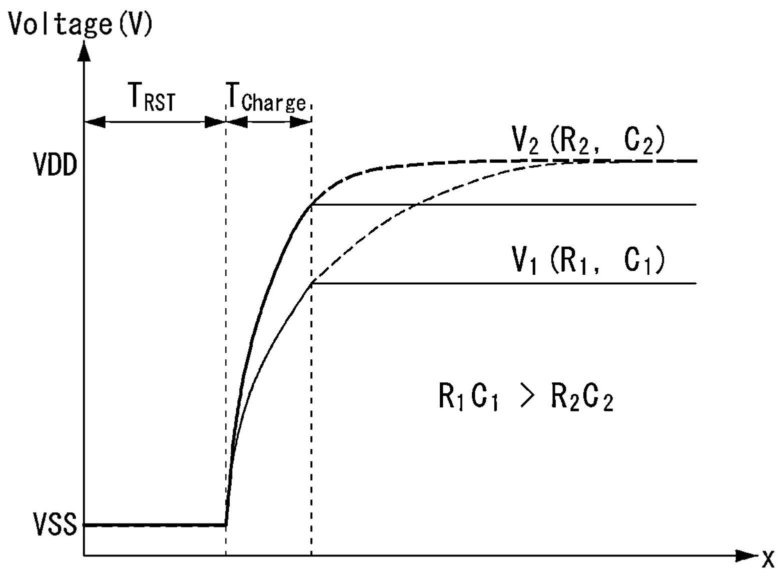
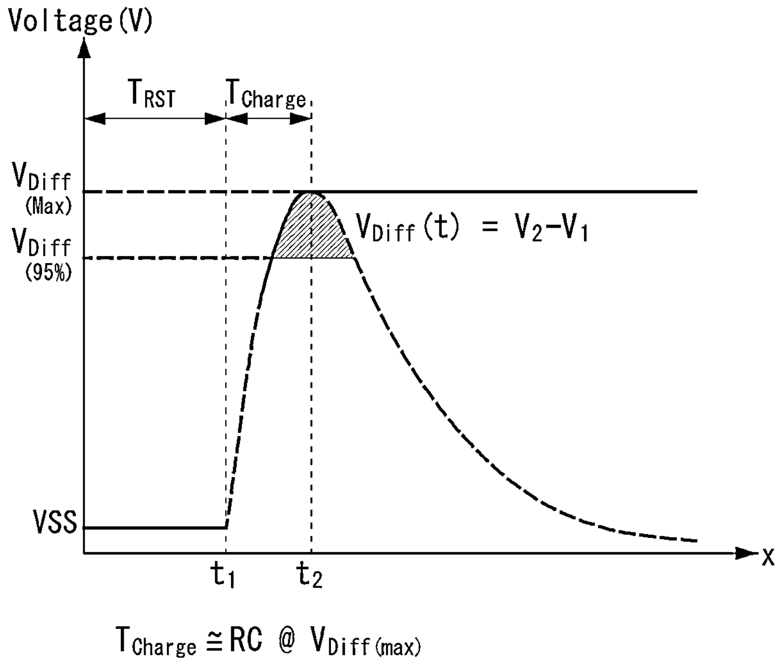

【FIG. 4】
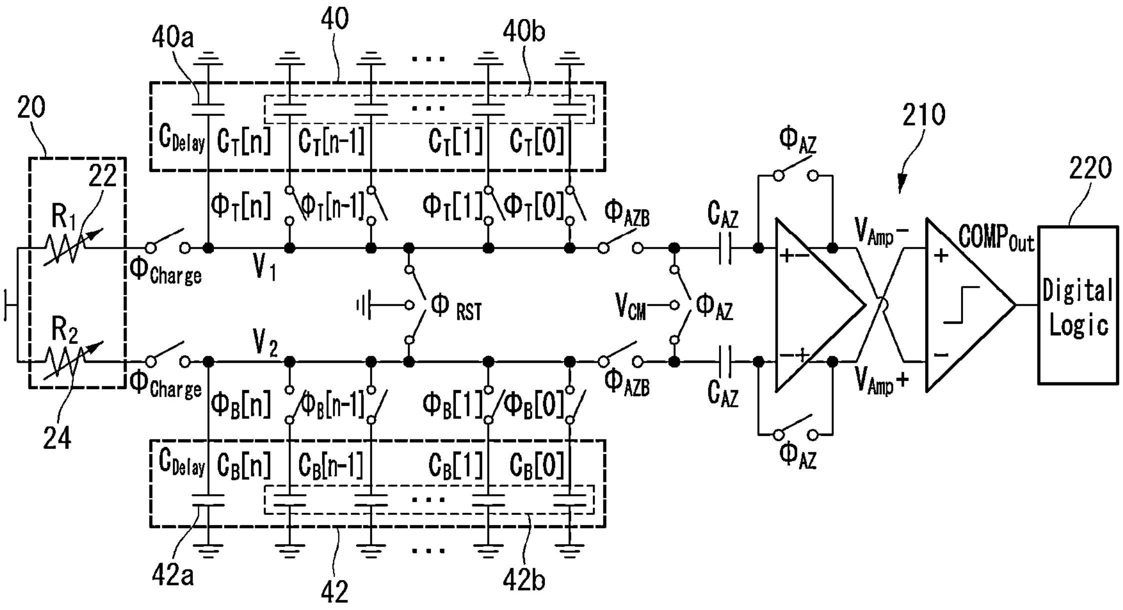
200

【FIG. 5】
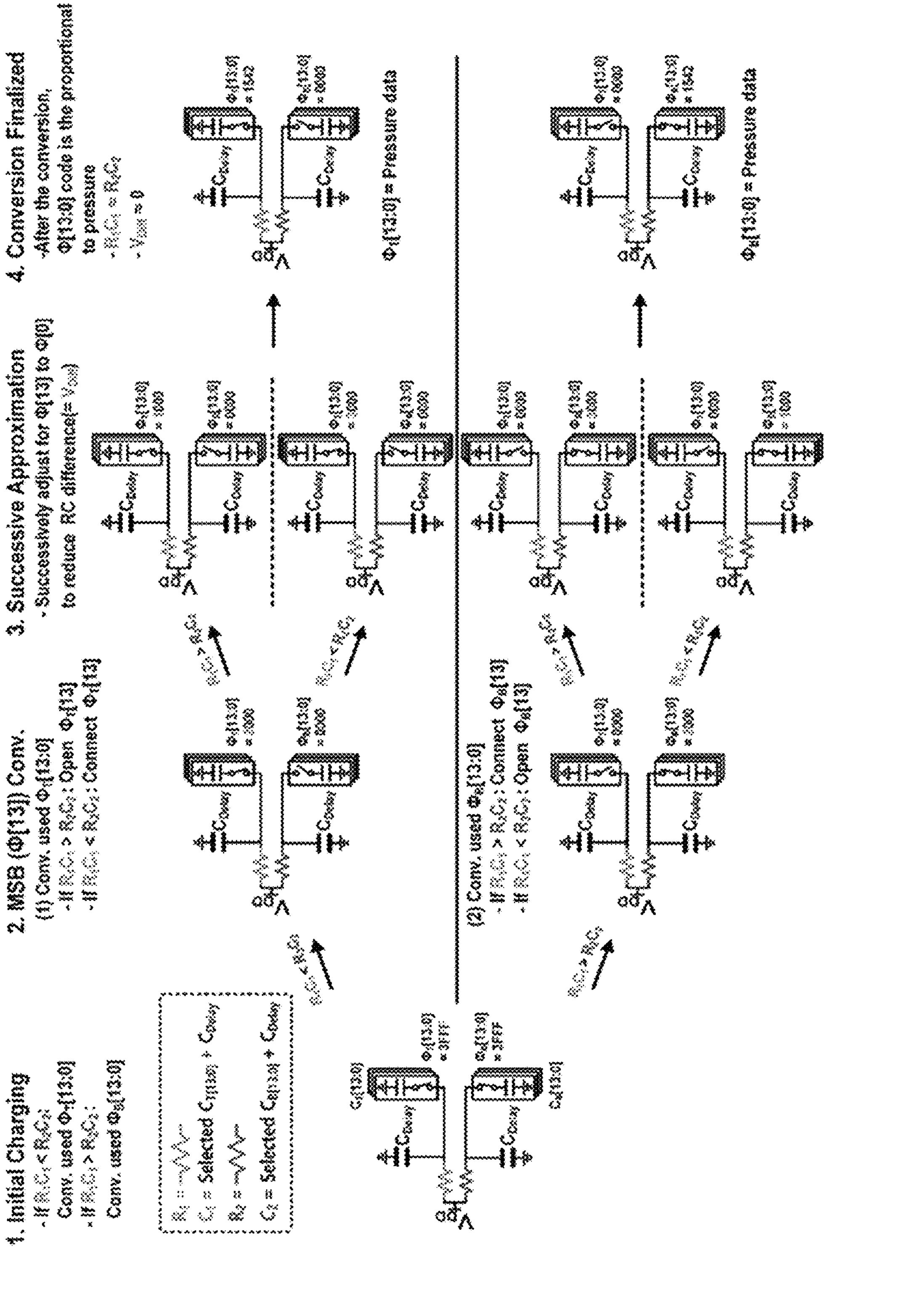

【FIG. 6】
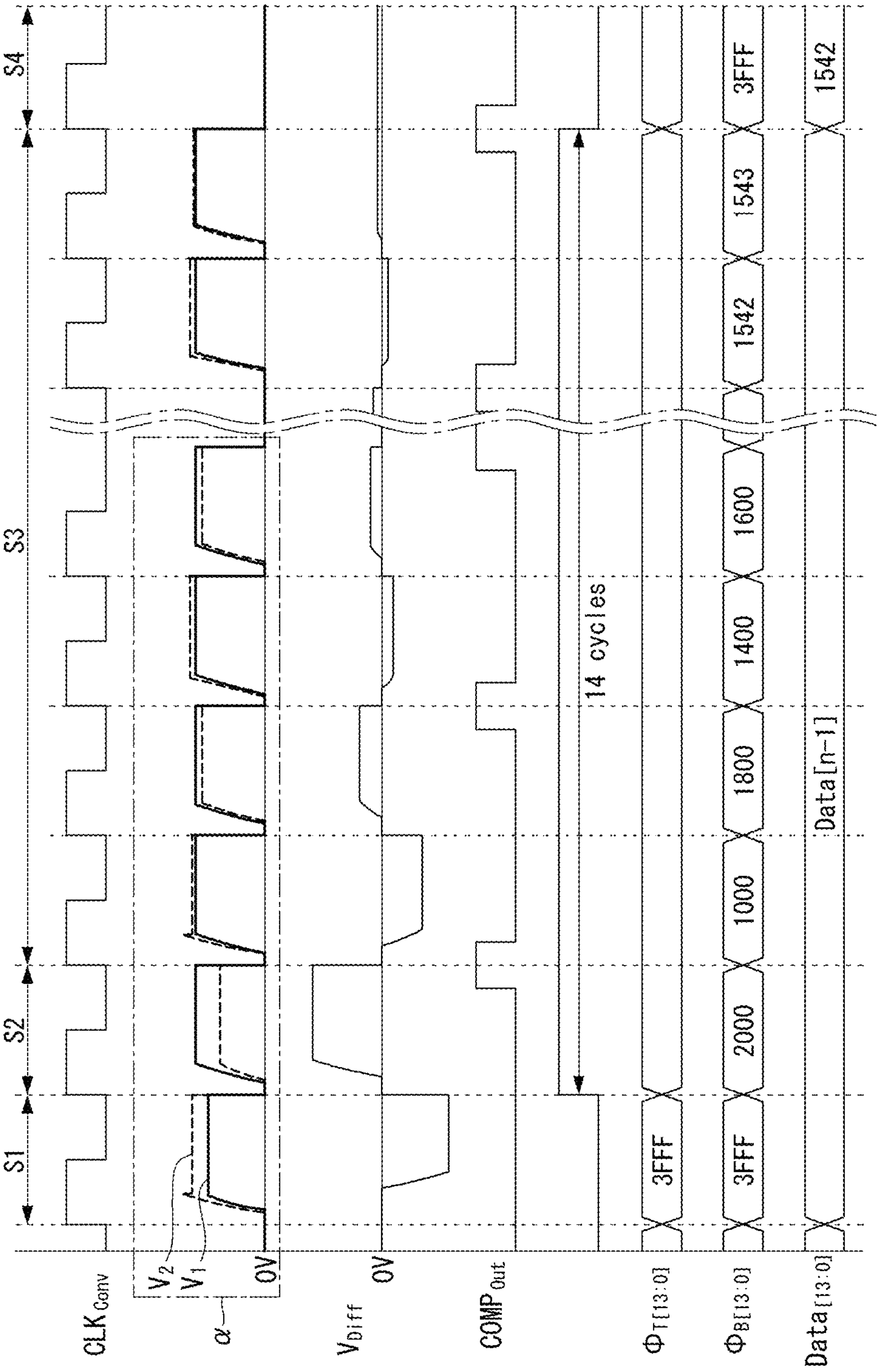

【FIG. 7】
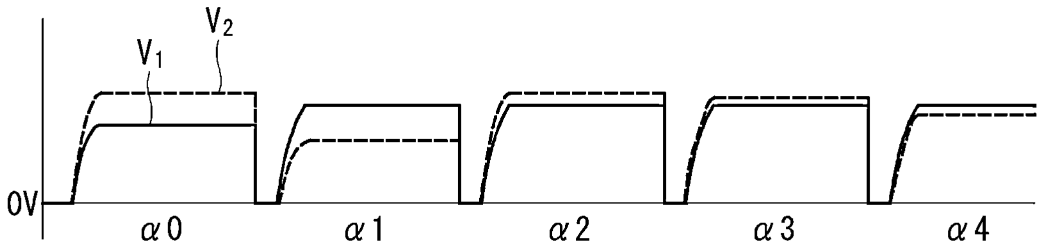

INTRAOCULAR PRESSURE SENSING DEVICE AND METHOD USING SENSOR BASED ON HALF WHEATSTONE BRIDGE

CROSS REFERENCE TO RELATED APPLICATIONS

This application claims the benefit under 35 USC § 119(a) of Korean Patent Application No. 10-2022-0081976, filed on Jul. 4, 2022, the entire disclosure of which is incorporated herein by reference for all purposes.

BACKGROUND

Field

The present disclosure relates to a device and a method for sensing intraocular pressure using a sensor based on a half Wheatstone bridge, and more particularly, to a device and a method for sensing intraocular pressure, which measure pressure through an RC delay comparison method using a half Wheatstone bridge constituted by two resistors.

Related Art

Glaucoma as a progressive ophthalmic nerve disease that causes vision damage is a disease in which early detection and appropriate treatment are required. In the onset and progress of glaucoma, among risk factors, especially, intraocular pressure is proven to be a core target of treatment. The intraocular pressure fluctuates during the day, and the larger a fluctuation width, the greater the risk of glaucoma progression. Therefore, continuous real-time intraocular pressure measurement is required for diagnosis and progression evaluation of glaucoma, but clinically widely used intraocular pressure meters have a limit that it is impossible to measure the intraocular pressure in real time.

As a transplanted intraocular pressure sensor is developed, power and data are delivered through a wireless signal to measure the pressure and temperature of an eyeball, and measured data can be stored and a signal measured by the sensor can be controlled by using a digital controller mounted inside a chip, but in the case of an intraocular pressure measurement method using chip transplantation of such a scheme, the sensor basically needs to be directly inserted into the eyeball, so miniaturization of the chip is required.

In order to enable the intraocular pressure to be monitored through a transplanted pressure sensor, the smaller the size of the sensor measuring the pressure, the more advantageous it will be, and it is necessary to provide a significant level of low power sensing system.

FIG. 1A is a circuit diagram illustrating a conventional sensor system using a Wheatstone bridge sensor and an analog to digital converter (ADC).

In such a conventional sensor system, the Wheatstone bridge sensor causes loss of energy and power due to a short circuit current pass. In a low power system in an environment where the energy and the power are limited, instantaneous energy and power loss are fatal.

FIG. 1B is a diagram illustrating the circuit diagram of the Wheatstone bridge and an actual appearance of a representative sensor of the Wheatstone bridge.

Referring to a right diagram (10*s*) of FIG. 1B, the sensor includes four variable resistors 10 in which resistance values $R_1$ to $R_4$ are varied according to various environmental changes including a temperature and pressure, and is a sensor 10*s* generally frequently used. In a general exemplary embodiment, the size of the sensor is 1 mm×1 mm×0.4 mm, and the sensitivity of the sensor has 20 μV/V/mmHg.

FIG. 1C is a diagram illustrating a circuit that converts a voltage generated by using a Wheatstone bridge (full-bridge) based sensor into a digital signal according to a conventional exemplary embodiment.

A voltage generated by a Wheatstone bridge (full-bridge) 10 is converted into data representing information on a current environment, and in this case, a capacitor $C_s$ next to the Wheatstone bridge 10 is used for a purpose of storing the voltage generated by the Wheatstone bridge 10.

In order to constantly and easily monitor the intraocular pressure by attaching the sensor using an internal space of a glaucoma implant, the miniaturization of the intraocular pressure measurement sensor and an ultra-low power sensing system are required to have a better advantage compared to the prior art as described above.

SUMMARY

The present disclosure is contrived to solve the problem in the related art, and the present disclosure provides a device and a method for sensing pressure, which use a Wheatstone bridge sensor for more miniaturization of an intraocular pressure sensor and measure pressure through an RC delay comparison method for a low-power operation.

According to a first aspect of the present disclosure, provided is a pressure sensing device using a sensor based on a Wheatstone bridge, which includes: a half Wheatstone bridge unit including two variable resistors of which resistance values are changed according to an environmental change; a variable capacitor unit electrically connected to the half Wheatstone bridge unit and generating RC delays for two variable resistors, respectively; an amplifier amplifying respective charging voltages charged after a time of the respective RC delays; and a comparator comparing the amplified charging voltages and outputting the compared charging voltages as digital values.

According to a second aspect of the present disclosure, provided is a pressure sensing method of a sensing device based on a Wheatstone bridge, in which the sensing device includes a half Wheatstone bridge unit including two variable resistors of which resistance values are changed according to an environmental change and a variable capacitor unit electrically connected to the half Wheatstone bridge unit, and the pressure sensing method includes: generating, by the variable capacitor unit, each of RC delays for the two variable resistors; an amplifier amplifying respective charging voltages charged after a time of the respective RC delays; and comparing the amplified charging voltages and outputting the compared charging voltages as digital values.

According to a third aspect of the present disclosure, provided is an implant for treating an eye disease, which includes: a distal portion including a snorkel having a size accommodated in a front of an eyeball; a proximal portion extended from the distal portion at an angle and having a shape accommodated in a part of a Schlemm's canal; and the pressure sensing device of the first aspect.

A device and a method for sensing pressure using a sensor based on a Wheatstone bridge according to exemplary embodiments of the present disclosure provide the following effects.

The device and the method for sensing pressure using a sensor based on a Wheatstone bridge according to exemplary embodiments of the present disclosure are efficient because the volume of a sensor is smaller and the number of resistors is smaller as compared with a case of using a full-bridge sensor constituted by four resistors by using a half Wheatstone bridge sensor constituted by two resistors.

In connection with the sensitivity of the sensor, by using RC delay as a charging voltage comparison method through a variable capacitor unit, a difference in microscopic resistance generated by environmental changes including pressure is detected by a scheme of comparing a difference in time occurring through the RC delay using a capacitor unit as accurately as possible, so it is possible to maintain a quality of a measurement pressure resolution even though the half Wheatstone bridge is used.

In individual switchings for a plurality of compensation capacitors of the variable capacitor unit, a parasitic capacitance is performed by using a predetermined switch so that capacities of capacitors at both ends of a switch are the same as each other, thereby guaranteeing the linearity and reliability of pressure digital conversion.

In outputting a digital value, as a weight is granted to the number of oversampling repetition times in a bit with a lot of errors in the bit position of CDAC, oversampling is performed, so less energy and time are consumed in terms of achievement of the measurement pressure resolution.

BRIEF DESCRIPTION OF THE DRAWINGS

FIG. 1A is a circuit diagram illustrating a conventional sensor system using a Wheatstone bridge sensor and an analog to digital converter (ADC).

FIG. 1B is a diagram illustrating the circuit diagram of the Wheatstone bridge and an actual appearance of a representative sensor of the Wheatstone bridge.

FIG. 1C is a diagram illustrating a circuit that converts a voltage generated by using a Wheatstone bridge (full-bridge) based sensor into a digital signal according to a conventional exemplary embodiment.

FIG. 2A is a diagram illustrating a half Wheatstone bridge circuit diagram and an actual appearance of a half Wheatstone bridge sensor according to a disclosed exemplary embodiment.

FIG. 2B is a diagram illustrating a circuit that converts a voltage generated by using a half Wheatstone bridge sensor into a digital signal according to a disclosed exemplary embodiment.

FIG. 3 is a graph for describing a principle of a point where a difference in RC delay becomes the maximum in an RC delay comparison method using a half Wheatstone bridge sensor according to a disclosed exemplary embodiment.

FIG. 4 is a diagram illustrating a pressure sensing device using a half Wheatstone bridge sensor according to a disclosed exemplary embodiment.

FIG. 5 is a diagram for sequentially describing a process of performing RC delay comparison for data conversion according to a disclosed exemplary embodiment.

FIG. 6 is a diagram illustrating, as a graph, a process of converting data through RC delay comparison according to a disclosed exemplary embodiment.

FIG. 7 is a diagram illustrating a charging voltage comparison method through capacitance change of a variable capacitor unit according to a disclosed exemplary embodiment.

DESCRIPTION OF EXEMPLARY EMBODIMENTS

Hereinafter, the present disclosure will be described in detail with reference to exemplary embodiments and drawings. However, in the following description, the present disclosure is not limited to a specific exemplary embodiment, but in describing the present disclosure, a detailed description of related known technologies will be omitted if it is determined that the detailed description may make the gist of the present disclosure unclear.

FIG. 2A is a diagram illustrating a half Wheatstone bridge circuit diagram and an actual appearance of a half Wheatstone bridge sensor according to a disclosed exemplary embodiment.

The half Wheatstone bridge sensor is a sensor 20*s* including two variable resistors 20 in which resistance values of $R_1$ and $R_2$ are changed according to changes of various environments including a temperature and pressure. The sensor 20*s* has an advantage of a smaller volume than the sensor 10*s* of FIG. 1B, but has a problem in that the sensitivity of the half Wheatstone bridge sensor 20*s* is lowered as compared with the Wheatstone bridge sensor 10*s* having relatively four resistors 10 in relation to a physical size.

In a disclosed exemplary embodiment, the half Wheatstone bridge sensor 20*s* may have a size of 0.9 mm×0.33 mm×0.18 mm, and have a sensitivity of 10 μV/V/mmHg.

FIG. 2B is a diagram illustrating a circuit that converts RC delay generated by using a half Wheatstone bridge sensor into a digital signal according to a disclosed exemplary embodiment.

Referring back to FIG. 1C, the circuit using the Wheatstone bridge (full-bridge) based sensor in the related art and the circuit of the disclosed exemplary embodiment are compared as follows.

The circuit using the Wheatstone bridge (full-bridge) based sensor in the related art stores a voltage generated by the Wheatstone bridge (full-bridge) 10 in a capacitor $C_s$ next to the full-bridge 10. The voltage stored in the capacitor $C_s$ is related to data.

On the contrary, the circuit 200 using the half Wheatstone bridge sensor according to the disclosed exemplary embodiment uses a technique of generating and utilizing the RC delay by using $R_1$ 22 and $R_2$ 24, which are resistors of the half Wheatstone bridge 20, and variable capacitors $C_1$ 40 and $C_2$ 42. Two RC delays have the same value by a scheme of compensating for a difference between RC delays generated by $R_1$ 22 and $R_2$ 24 by changing capacitance values of $C_1$ 40 and $C_2$ 42. In this process, depending on the degree of the compensation, digital data that represents various environmental information including the temperature and the pressure may be obtained.

In the disclosed exemplary embodiment, the pressure sensing device 200 using the Wheatstone bridge based sensor may include a half Wheatstone bridge unit 20 including two variable resistors in which resistance values are changed according to an environmental change, variable capacitor units 40 and 42 electrically connected to the half Wheatstone bridge unit 20 and generating the RC delays for two variable resistors 22 and 24, respectively, an amplifier 210 amplifying a difference between respective charging voltages charged after the respective generated RC delay time, and a comparator 220 comparing the amplified charging voltages and outputting the magnitude of delay time of charging voltages as digital values.

Meanwhile, in the disclosed exemplary embodiment, a process that makes two RC delays have the same value may be conducted by a scheme of changing the capacitances of the variable capacitor units 40 and 42 related to the RC delays generated to have the amplified charging voltages, and outputting the digital values based on the changed capacitances.

FIG. 3 is a graph for describing a principle of a point where a difference of RC delay becomes the maximum in an RC delay comparison method using a half Wheatstone bridge sensor according to a disclosed exemplary embodiment.

As described above, the half Wheatstone bridge sensor has a smaller volume than a general Wheatstone bridge sensor, but is disadvantageous in terms of the sensitivity of the sensor itself, so a resolution may deteriorate at the time of measuring the environments such as the pressure and the temperature, and in order to overcome the deteriorated resolution, a technique is used, which is capable of more easily distinguishing a difference in resistance through the RC delay using the capacitor with respect to a small resistance difference by generating the RC delay. As a result, a method is required, which may compare RC delay values using the resistors $R_1$ 22 and $R_2$ 24 of the half Wheatstone bridge 20 and the variable capacitors $C_1$ 40 and $C_2$ 42 may be compared as accurately as possible.

An equation of analyzing the RC delay charging voltage generated by the difference between the resistance values $R_1$ and $R_2$ is described below.

$$V_{Diff}(t) = \left\{\left(1-\exp\left(\frac{-t}{R_2\cdot C_2}\right)\right)\right\} - \left\{\left(1-\exp\left(\frac{-t}{R_1\cdot C_1}\right)\right)\right\} \quad \text{[Equation 1]}$$

$$V'_{Diff}(t) = \frac{1}{R_2\cdot C_2}\cdot\exp\left(\frac{-t}{R_2\cdot C_2}\right) - \frac{1}{R_1\cdot C_1}\cdot\exp\left(\frac{-t}{R_1\cdot C_1}\right) \quad \text{[Equation 2]}$$

$$V_{Diff}(t) \text{ is maximize at } V'_{Diff}(t_{max}) = 0 \quad \text{[Equation 3]}$$

$$\text{Assuming, } \begin{cases} R \gg \Delta R,\ \Delta R = \text{pressure term in Res.} \\ R_1 = R + \Delta R,\ R_2 = R - \Delta R,\ R_1 > R_2 \\ C \approx C_1 \approx C_2 \end{cases} \quad \text{[Equation 4]}$$

$$\text{Optimal } T_{Charge} = \frac{C\cdot R_2\cdot R_1\cdot\ln\left(\frac{R_2}{R_1}\right)}{R_2 - R_1} = \frac{C\cdot(R+\Delta R)\cdot(R-\Delta R)\cdot\ln\left(\frac{R+\Delta R}{R-\Delta R}\right)}{2\cdot\Delta R} \approx RC \quad \text{[Equation 5]}$$

According to the equations, since a time point when the difference between the RC delays becomes the maximum coincides with a time constant, when the voltages charged in the capacitor units 40 and 42 are compared by stopping charging after charging only for a time which is as much as the time constant, it is possible to accurately compare the charging voltages.

FIG. 4 is a diagram illustrating a pressure sensing device using a half Wheatstone bridge sensor according to a disclosed exemplary embodiment.

In the disclosed exemplary embodiment, the variable capacitor units 40 and 42 may include first and second variable capacitor units 40 and 42 electrically connected to first and second variable resistors 22 and 24 which are two variable resistors 20, respectively, and the first and second variable capacitor units 40 and 42 may include delay capacitors 40*a* and 42*a* each electrically connected one variable resistor and generating the RC delay, and one or more compensation capacitors 40*b* and 42*b* connected to the delay capacitors in parallel and compensating for the RC delay difference, respectively, and electrical connection of one or more respective compensation capacitors 40*b* and 42*b* to the delay capacitors may be independently controlled through individual switchings and $\Phi_T$[n] and, $\Phi_B$[n].

In a disclosed exemplary embodiment illustrated in FIG. 4, a capacitance of a variable capacitor $C_1$ 40 becomes a sum of capacitances $C_{Delay}$ and $C_T$[0] to $C_T$[n] (hereinafter, referred to as $C_T$[n:0]), and similarly, a capacitance of a variable capacitor $C_2$ 42 becomes a sum of capacitances $C_{Delay}$ and $C_B$[0] to $C_B$[n] (hereinafter, referred to as $C_B$[n:0]). $C_{Delay}$ corresponds to a core element of generating the RC delay, and then, compensates for a difference in RC delays generated by $R_1$ and $R_2$, respectively by using $C_T$[n:0] or $C_B$[n:0] through switching.

$C_T$[n:0] and $C_B$[n:0] have binary sizes in which the capacitance is doubled toward a most significant bit (MSB) from a lowest significant bit (LSB). For example, a capacitance of C[0]=C has C[1]=2C and C[2]=4C, and in the case of an analog digital converter (ADC), the MSB has a capacitance of $2^{n-1}$C.

FIG. 5 is a diagram for sequentially describing a process of performing RC delay comparison for data conversion according to a disclosed exemplary embodiment.

In a disclosed exemplary embodiment, first, initial charging is made in a state in which individual switchings $\Phi_T$[n] and $\Phi_B$[n] of a plurality of compensation capacitors 40*b* and 42*b* are all turned on. A larger value is determined by comparing $\tau_1=R_1C_1$ and $\tau_2=R_2C_2$. When $\tau_1>\tau_2$, an operation of the pressure sensing device 200 is made by a scheme in which $\tau_2$ is matched by using the compensation capacitor $C_B$[n] based on $\tau_1$, and when $\tau_2>\tau_1$, the operation of the pressure sensing device 200 is made by a scheme in which $\tau_1$ is matched by using the compensation capacitor $C_T$[n] based on $\tau_2$.

When a compensation capacitor group to be used among the compensation capacitors $C_T$[n] 40*b* and $C_B$[n] 42*b* is determined (in other words, when one of $C_T$[n] 40*b* and $C_B$[n]42*b* is determined), data conversion starts. In the disclosed exemplary embodiment, the compensation capacitors $C_T$[n] 40*b* and $C_B$[n] 42*b* are exclusively used, and for example, if $C_B$[n] is used, the data conversion may be conducted by using a binary search method by a scheme of comparing a value of $\tau_2=R_2C_2$ with $\tau_1$ by setting a reference RC delay as $\tau_1=R_1C_{Delay}$ without using $C_T$[n].

Referring to FIG. 5, in an exemplary embodiment, when $C_B$[13:0] is used, the switch $\Phi_B$[13] connected to the capacitor of $C_B[13]=2^{13}C$ is turned on to generate the RC delay of $\tau_2=R_2(C_{Delay}+2^{13}C)$. $\tau_1$ and $\tau_2$ are compared, and when a value of $\tau_2$ is larger, the switch $\Phi_B$[13] is turned off and $\Phi_B$[12] is turned on, and $\tau_2=R_2(C_{Delay}+2^{12}C)$ is set to decrease $\tau_2$. On the contrary, the data conversion may be conducted by using a binary search method by a scheme of increasing a delay of $\tau_2$ by generating the RC delay with $\tau_2=R_2(C_{Delay}+2^{13}C+2^{12}C)$ by maintaining the switch $\Phi_B$[13] in a turn-on state and additionally turning on even $\Phi_B$[12] when the value of $\tau_2$ is smaller.

FIG. 6 is a diagram illustrating, as a graph, a process of converting data through RC delay comparison according to a disclosed exemplary embodiment.

Referring back to FIG. 3, it may be identified that in $\tau_1=R_1C_1$ and $\tau_2=R_2C_2$, as the value of $\tau$ is larger, a voltage value becomes smaller, and as a result, in the disclosed exemplary embodiment, respective charging voltages charged after an RC delay time amplified through an amplifier 210 may be compared through a comparator 220.

In FIG. 6, the charging voltages correspond to $V_1$ and $V_2$ and for example, when $V_1>V_2$, $\tau_1<\tau_2$ and when $V_1<V_2$, $\tau_1>\tau_2$. In an exemplary embodiment, in the case of $V_1<V_2$ in the voltage generated by conducting the RC charging, $\tau_2$ is smaller, so a process of adjusting the RC delay by adding the compensation capacitor by using the switch $\Phi_B$[13:0] which affects generation of $V_2$ may be conducted. In this case, $V_1$ is fixed to $\tau_1=R_1C_{Delay}$, so $V_1$ becomes a reference voltage and a reference RC delay, and $\tau_2$ becomes $\tau_1$ through a binary search process.

When an exemplary embodiment of the binary search process is described in more detail, first, the switch $\Phi_B[13]$ connected to the capacitor of $C_B[13]=2^{13}C$ is turned to generate the RC delay of $\tau_2=R_2(C_{Delay}+2^{13}C)$. When $V_1$ and $V_2$ are compared, if a value of $V_2$ is smaller, the switch $\Phi_B[13]$ is turned off and the switch $\Phi_B[12]$ is turned on to generate the RC delay with $\tau_2=R_2(C_{Delay}+2^{12}C)$, and then the comparison is repeated again. When $V_1$ and $V_2$ are compared again, if the value of $V_2$ is larger at this time, the switch $\Phi_B[12]$ is maintained in the turn-on state, and then the switch $\Phi_B[11]$ is turned on, and the comparison is continuously conducted, and such a process is repeatedly performed.

FIG. 7 is a diagram illustrating a charging voltage comparison method through capacitance change of a variable capacitor unit according to a disclosed exemplary embodiment.

FIG. 7 is an enlarged diagram of a graph part a related to charging voltages $V_1$ and $V_2$, and hereinafter, a digital conversion process of data according to an exemplary embodiment will be summarized and described in detail with reference to FIG. 7.

(i) $\Phi_B[13]$ turn-on state ($\alpha 1$)

Since $V_1>V_2\tau_1=R_1C_{Delay}<\tau_2=R_2(C_{Delay}+2^{13}C)$. Therefore, the switch $\Phi_B[13]$ should be changed to turn-off, and an output of 13 bits becomes 0.

(ii) $\Phi_B[13]$ turn-off state and $\Phi_B[12]$ turn-on state ($\alpha 2$)

Since $V_1<V_2$, $\tau_1=R_1C_{Delay}>\tau_2=R_2(C_{Delay}+2^{12}C)$. Therefore, the switch $\Phi_B[12]$ is maintained in the turn-on state, and an output of 12 bits becomes 1.

(iii) $\Phi_B[13]$ turn-off state, $\Phi_B[12]$ turn-on state, and $\Phi_B[11]$ turn-on state ($\alpha 3$)

Since $V_1<V_2$, $\tau_1=R_1C_{Delay}>\tau_2=R_2(C_{Delay}+2^{12}C+2^{11}C)$. Therefore, the switch $\Phi_B[11]$ is maintained in the turn-on state, and an output of 11 bits becomes 1.

(iv) $\Phi_B[13]$ turn-off state, $\Phi_B[12]$ turn-on state, $\Phi_B[11]$ turn-on state, and $\Phi_B[10]$ turn-on state ($\alpha 4$)

Since $V_1>V_2$, $\tau_1=R_1C_{Delay}<\tau_2=R_2(C_{Delay}+2^{12}C+2^{11}C+2^{10}C)$. Therefore, the switch $\Phi_B[10]$ should be changed to turn-off, and an output of 10 bits becomes 0.

For reference, in a state ($\alpha 0$) of a graph before the $\Phi_B[13]$ turn-on state ($\alpha 1$), in the case of $V_1<V_2$ in a voltage generated when the RC charging is conducted as described above, $\tau_2$ is smaller, so $V_1$ is fixed to $\tau_1=R_1C_{Delay}$, and becomes the reference voltage and the reference RC delay, which corresponds to an initial state in which $\tau_2$ becomes $\tau_1$ through the binary search process.

When the charging voltage comparison process is repeatedly performed, data from the most significant bit (MSB) to the lowest significant bit (LSB) are sequentially determined through comparison of sizes of the RC delays, and conversion of environmental data including the pressure and the temperature is completed after sequential switching.

In the disclosed exemplary embodiment, in respect to the switches $\Phi_T[n]$ and $\Phi_B[n]$ of the variable capacitor unit, a switch in which a parasitic capacitance is constant may be used so that capacities of capacitors the same as each other at both ends. Through this, the accuracy of the RC delay through the charging voltage may be further increased.

In the disclosed exemplary embodiment, bit-level oversampling used for the digital conversion of the data may be performed by granting a weight to the number of oversampling repetition times in a binary bit digit in which the error intensively occurs by comparison with the number of oversampling repetition times in a binary bit digit in which the error does not occur through statistical analysis. As a result, efficiency may be improved in terms of energy and time.

Meanwhile, an implant for treating an eye disease according to a general exemplary embodiment may include a distal portion including a snorkel having a size accommodated in a front of an eyeball and a proximal portion extended from the distal portion at an angle and having a shape accommodated in a part of a Schlemm's canal, and here, a pressure sensing device 200 using a half Wheatstone bridge sensor according to an additionally disclosed exemplary embodiment may be included inside the implant.

As such, there is an effect in that the intraocular pressure sensing device is further minimized and has smaller power loss through the device and the method for sensing the pressure, which measure the pressure by using the RC delay comparison method with the half Wheatstone bridge sensor.

Since various modified examples can be made by a configuration and a method described and exemplified in the present disclosure without departing from the scope of the present disclosure, all matters included in the detailed description or illustrated in the accompanying drawings are illustrative and do not limit the present disclosure. Accordingly, the scope of the present disclosure is not limited by the exemplary embodiment, but should be defined only according to the following claims and equivalents thereto.

What is claimed is:

1. A pressure sensing device using a sensor based on a Wheatstone bridge, comprising:

a half Wheatstone bridge unit including two variable resistors of which resistance values are changed according to an environmental change;

a variable capacitor unit electrically connected to the half Wheatstone bridge unit and generating RC delays for two variable resistors, respectively;

an amplifier amplifying respective charging voltages charged after a time of the respective RC delays; and a comparator comparing the amplified charging voltages and outputting the compared charging voltages as digital values.

2. The pressure sensing device of claim 1, wherein a capacitance of the variable capacitor unit is changed based on the generated RC delay so that the amplified charging voltages have the same value, and the digital value is output based on the changed capacitance.

3. The pressure sensing device of claim 1, wherein the variable capacitor unit includes first and second variable capacitor units electrically connected to first and second variable resistors which are two variable resistors, respectively, wherein each of the first and second variable capacitors includes a delay capacitor electrically connected to one variable resistor and generating the RC delay, and one or more compensation capacitors connected to the delay capacitor in parallel, and compensating for an RC delay difference, and wherein an electrical connection of each of one or more compensation capacitors to the delay capacitor is independently controlled through individual switchings.

4. The pressure sensing device of claim 3, wherein the one or more compensation capacitors are a plurality of compensation capacitors, wherein the plurality of compensation capacitors are configured so that capacitances sequentially have values doubled based on a capacitance of a compensation capacitor having a smallest capacitance, and wherein the digital value is output based on combination of the individual switchings.

5. The pressure sensing device of claim 4, wherein in a state which the individual switches of the compensation capacitors are all turned on, RC charging is performed, and wherein after the RC charging is performed, a first RC delay value which is a multiplication of a value of the first variable resistor and a value of the first variable capacitor unit, and a second RC delay value which is a multiplication of a value of the second variable resistor and a value of the second variable capacitor unit are compared to output the digital value based on a combination of the individual switchings of the first or second variable capacitor unit corresponding to a smaller RC delay value.

6. The pressure sensing device of claim 5, wherein in the case of the comparison of the amplified charging voltages, the first and second RC delay values are compared, and the digital value is output based on the combination of the individual switchings, which allows the charging voltage having the smaller RC delay value to have the same value as the charging voltage having the larger RC delay value.

7. The pressure sensing device of claim 4, wherein the output of the digital value is output as 1 when the individual switchings are turned on and 0 when the individual switchings are turned off as binary bits are determined based on the capacitances of the plurality of respective compensation capacitors.

8. The pressure sensing device of claim 3, wherein the individual switchings are performed by using a constant switch by a parasitic capacitance so that capacities of capacitors are the same as each other at both ends of the switch.

9. The pressure sensing device of claim 1, wherein the output as the digital value by comparing the amplified charging voltages by the comparator is performed by granting a weight to a number of oversampling repetition times in a bit with a lot of errors in a bit position of a capacitive digital-to-analog converter (CDAC).

10. A pressure sensing method of a sensing device based on a Wheatstone bridge, wherein the sensing device includes a half Wheatstone bridge unit including two variable resistors of which resistance values are changed according to an environmental change and a variable capacitor unit electrically connected to the half Wheatstone bridge unit, and wherein the pressure sensing method includes, generating, by the variable capacitor unit, each of RC delays for the two variable resistors;

an amplifier amplifying respective charging voltages charged after a time of the respective RC delays; and comparing the amplified charging voltages and outputting the compared charging voltages as digital values.

11. The pressure sensing method of claim 10, wherein a capacitance of the variable capacitor unit is changed based on the generated RC delay so that the amplified charging voltages have the same value, and the digital value is output based on the changed capacitance.

12. The pressure sensing method of claim 10, wherein the variable capacitor unit includes first and second variable capacitor units electrically connected to first and second variable resistors which are two variable resistors, respectively, wherein the first and second variable capacitor units include a delay capacitor and one or more compensation capacitors, respectively, wherein the generating of the RC delay is performed so that the delay capacitor is electrically connected to the first or second variable resistor to generate the RC delay, and wherein in the outputting as the digital values, each of the one or more compensation capacitors is connected to the delay capacitor in parallel, and electrical connection is independently controlled through individual switchings to compare the amplified charging voltages by a scheme of compensating for an RC delay difference.

13. The pressure sensing method of claim 12, wherein the one or more compensation capacitors are a plurality of compensation capacitors, wherein the plurality of compensation capacitors are configured so that capacitances sequentially have values doubled based on a capacitance of a compensation capacitor having a smallest capacitance, and wherein the outputting as the digital values is performed based on a combination of the individual switchings.

14. The pressure sensing method of claim 13, wherein the generating of each of the RC delays includes in a state in which the individual switchings of the plurality of compensation capacitors are all turned on, performing RC charging, and comparing a first RC delay value which is a multiplication of a value of the first variable resistor and a value of the first variable capacitor unit and a second RC delay value which is a multiplication of a value of the second variable resistor and a value of the second variable capacitor unit after performing the RC charging, and wherein the outputting as the digital values is performed based on a combination of the individual switchings of the first or second variable capacitor unit corresponding to a smaller RC delay value.

15. The pressure sensing method of claim 14, wherein the outputting as the digital values is performed based on the combination of the individual switching, which allows the charging voltage having the smaller RC delay value to have the same value as a charging voltage having a larger RC delay value.

16. The pressure sensing method of claim 13, wherein in the outputting as the digital values, the digital value is output as 1 when the individual switchings are turned on and 0 when the individual switchings are turned off as binary bits are determined based on the capacitances of the plurality of respective compensation capacitors.

17. The pressure sensing method of claim 12, wherein the individual switchings are performed by using a constant switch by a parasitic capacitance so that capacities of capacitors are the same as each other at both ends of the switch.

18. The pressure sensing method of claim 10, wherein the outputting as the digital values is performed by granting a weight to a number of oversampling repetition times in a a bit with a lot of errors in a bit position of a capacitive digital-to-analog converter (CDAC).

19. An implant for treating an eye disease, comprising:

a distal portion including a snorkel having a size configured to be accommodated in a front of an eyeball;

a proximal portion extended from the distal portion at an angle and having a shape configured to be accommodated in a part of a Schlemm's canal; and a pressure sensing device using a sensor based on a Wheatstone bridge, the pressure sensing device including:

a half Wheatstone bridge unit including two variable resistors of which resistance values are changed according to an environmental change;

a variable capacitor unit electrically connected to the half Wheatstone bridge unit and generating RC delays for two variable resistors, respectively; and an amplifier amplifying respective charging voltages charged after a time of the respective RC delays.

* * * * *